US009295831B2

(12) United States Patent
Hagr et al.

(10) Patent No.: US 9,295,831 B2
(45) Date of Patent: Mar. 29, 2016

(54) ELECTRODE WITH ANTI-SPRING BACK COMPONENT

(71) Applicant: MED-EL Elektromedizinische Geraete GmbH, Innsbruck (AT)

(72) Inventors: Abdulrahman Abdullah Hagr, Riyadh (SA); Anandhan Dhanasingh, Innsbruck (AT); Claude Jolly, Innsbruck (AT); Roland Hessler, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/618,000

(22) Filed: Feb. 10, 2015

(65) Prior Publication Data

US 2015/0224300 A1 Aug. 13, 2015

Related U.S. Application Data

(60) Provisional application No. 61/938,308, filed on Feb. 11, 2014, provisional application No. 61/987,568, filed on May 2, 2014.

(51) Int. Cl.
*A61N 1/00* (2006.01)
*A61N 1/05* (2006.01)

(52) U.S. Cl.
CPC .................................. *A61N 1/0541* (2013.01)

(58) Field of Classification Search
CPC ........................ A61N 1/0541; A61N 1/36032
See application file for complete search history.

(56) References Cited

U.S. PATENT DOCUMENTS

| 4,706,682 A | 11/1987 | Stypulkowski et al. |
| 6,266,568 B1 | 7/2001 | Mann et al. |
| 6,397,110 B1 * | 5/2002 | Kuzma ................. A61N 1/0541 607/137 |

(Continued)

FOREIGN PATENT DOCUMENTS

| EP | 1004326 A2 | 5/2000 |
| EP | 0966310 B1 | 2/2006 |
| WO | WO 2007/027879 | 3/2007 |
| WO | WO 2011/149695 | 12/2011 |

OTHER PUBLICATIONS

International Searching Authority, Authorized Officer Blaine R. Copenheaver, International Search Report and Written Opinion—PCT/US2015/015105, date of mailing May 18, 2015, 12 pages.

*Primary Examiner* — Robert N Wieland
(74) *Attorney, Agent, or Firm* — Sunstein Kann Murphy & Timbers LLP

(57) ABSTRACT

An implantable electrode arrangement for a cochlear implant system is described that prevents post-surgical retraction of the electrode. The arrangement includes at least one retraction limiter having an extracochlear portion located at a distal end of the extracochlear electrode lead and an intracochlear portion located at a proximal end of the intracochlear electrode array and made at least in part of a swellable material that expands in response to fluid contact. The intracochlear portion of the retraction limiter is adapted for deformation away from an outer surface of the array proximal end in response to exposure of the swellable material to perilymph fluid within the cochlea after surgical insertion of the electrode array into the implanted cochlea so as to form an anti-retraction projection preventing post-surgical retraction of the array proximal end back through the electrode opening in the outer surface of the implanted cochlea.

9 Claims, 9 Drawing Sheets

(56) References Cited

U.S. PATENT DOCUMENTS

| | | |
|---|---|---|
| 8,364,281 B2 | 1/2013 | Duncan et al. |
| 2002/0029074 A1 | 3/2002 | Treaba et al. |
| 2004/0236390 A1 | 11/2004 | Dadd et al. |
| 2008/0234793 A1 | 9/2008 | Gibson |
| 2009/0254163 A1 | 10/2009 | Gibson |
| 2012/0185028 A1 | 7/2012 | Gantz |
| 2013/0060260 A1 | 3/2013 | Dudziak et al. |
| 2013/0331779 A1 | 12/2013 | Dhanasingh et al. |
| 2014/0324069 A1* | 10/2014 | Gerber et al. .......... A61B 19/00 606/129 |
| 2015/0119967 A1* | 4/2015 | Pawsey .............. A61N 1/36032 607/137 |

\* cited by examiner

ELECTRODE WITH ANTI-SPRING BACK COMPONENT

This application claims priority from U.S. Provisional Patent Application No. 61/938,308, filed Feb. 11, 2014, and from U.S. Provisional Patent Application No. 61/987,568, filed May 2, 2014, both which are incorporated herein by reference in their entireties.

TECHNICAL FIELD

The present invention relates to medical implants, and more specifically to an implantable electrode arrangement for cochlear implant systems.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by an auditory prosthesis system such as a cochlear implant that electrically stimulates auditory nerve tissue with small currents delivered by multiple stimulation contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing such as error correction, pulse formation, etc., and produces a stimulation pattern (based on the extracted audio information) that is sent through an electrode lead 109 to an implanted electrode array 110 which penetrates into the cochlea 104 through a surgical opening in the outer surface of the cochlea 104. Typically, this electrode array 110 includes multiple stimulation contacts 112 on its surface that deliver the stimulation signals to adjacent neural tissue of the cochlea 104 which the brain of the patient interprets as sound. The individual stimulation contacts 112 may be activated sequentially, or simultaneously in one or more contact groups.

FIG. 2A shows structural details of a cochlear implant electrode arrangement at the electrode opening 201 into the cochlea 104. After the insertion procedure, the electrode array 110 tends to lie toward the outer lateral wall of the spiral-shaped cochlea 104. Over time, there can be a tendency for the electrode array to spring back and retract back out through the electrode opening 201, as shown in FIG. 2B. The degree of spring back varies depending on how deeply the electrode array 110 is inserted into the cochlea 104, how well the electrode opening 201 is packed with fascia material, and the specific geometry at the electrode opening 201.

Such post-surgical electrode retraction pulls the nearest stimulation contact 112 away from its intended target neural tissue within the cochlea 104 back toward the electrode opening 201, or even further, back outside the cochlea 104 into the middle ear 104. This can produce pain sensation in the patient when that stimulation contact 112 is energized. Usually in such circumstances, that stimulation contact 112 will be inactivated and fewer stimulation contacts 112 remain for use to produce sound sensation.

Various approaches have been attempted to resist such post-surgical retraction. A cork-shaped stopper has been used to tightly wedge the electrode lead in the electrode opening. An anti-retraction skirt has been implemented on the electrode array at the electrode opening which is made of polymer material that swells when contacted by the liquid preilymph medium, thereby holding the electrode array in place. Some electrode arrays have a permanent pre-curved shape that does not relax or spring back after insertion into the cochlea. Other electrode arrangements contain an internal malleable material on either side of the electrode opening which maintains a bent shape after full insertion of the electrode array to resist retraction. A surgical group in Hannover Germany has added to the implant electrode a wing of flexible silicone material that can be fixed to a groove in the bony material on the outer surface of the cochlea near the electrode opening. All of these efforts have suffered from various issues that leave each an imperfect solution.

SUMMARY

Embodiments of the present invention are directed to an implantable electrode arrangement for a cochlear implant system that prevents post-surgical retraction. An extracochlear electrode lead for carrying one or more cochlear stimulation signals has a proximal end couplable to an implanted signal processor and a distal end configured to enter an electrode opening in the outer surface of a cochlea. An intracochlear electrode array has an array proximal end connected to the lead distal end at the electrode opening, an array distal end terminating within the cochlea, and an outer surface with stimulation contacts for applying the cochlear stimulation signals to target neural tissue within the cochlea. The electrode arrangement also includes at least one retraction limiter The arrangement includes at least one retraction limiter having an extracochlear portion located at a distal end of the extracochlear electrode lead and an intracochlear portion located at a proximal end of the intracochlear electrode array and made at least in part of a swellable material that expands in response to fluid contact. The intracochlear portion of the retraction limiter is adapted for deformation away from an outer surface of the array proximal end in response to exposure of the swellable material to perilymph fluid within the cochlea after surgical insertion of the electrode array into the cochlea so as to form an anti-retraction projection preventing post-surgical retraction of the array proximal end back through the electrode opening in the outer surface of the cochlea.

In further specific embodiments, a distal end of the intracochlear portion of the at least one retraction limiter is fixedly attached to the outer surface of the array proximal end, and the remainder of the intracochlear portion is separable from the outer surface of the array proximal end. In that way, sliding of the extracochlear portion over the lead distal end causes the separable part of the intracochlear portion to deform out away from the outer surface of the array proximal end to form the anti-retraction projection. The extracochlear portion of the at least one retraction limiter may also be adapted for fixed attachment to the lead distal end after sliding.

In other specific embodiments, the at least one retraction limiter may include an internal stiffener channel configured to contain an insertion stiffener that holds the intracochlear portion of the retraction limiter straight against the outer surface of the array proximal end during surgical insertion of the electrode array into the cochlea, and configured to allow the intracochlear portion of the retraction limiter to deform away from the outer surface of the array proximal end to form the anti-retraction projection when the insertion stiffener is withdrawn from the stiffener channel after surgical insertion of the electrode array into the cochlea.

Or the intracochlear portion of the retraction limiter may be wedge-shaped, and the outer surface of the array proximal end may then include a corresponding wedge-shaped limiter receptacle adapted to contain the intracochlear portion during surgical insertion of the electrode array into the cochlea. The intracochlear portion then is adapted for sliding back out of the limiter receptacle towards the electrode opening after the surgical insertion to form the anti-retraction projection.

In any of the foregoing embodiments, there may also be an imaging marker configured to prominently indicate the electrode opening in post-surgical imaging of the electrode arrangement. The at least one retraction limiter may be formed of resilient silicone material. The retraction limiter may be at least in part formed or coated with a swellable material. In one embodiment, only the extracochlear portion or the intracochlear portion is at least in part formed or coated with a swellable material. The swellable material may be any material that expands in response to fluid contact. In some embodiments, there may be multiple retraction limiters.

Embodiments of the present invention also include a cochlear implant system having an electrode arrangement according to any of the foregoing.

DETAILED DESCRIPTION

Embodiments of the present invention are directed to a cochlear implant electrode with an anti-spring back retraction limiter structure at the electrode opening into the cochlea that resists post-surgical retraction of the inserted electrode back out of the electrode opening.

Figure 1:
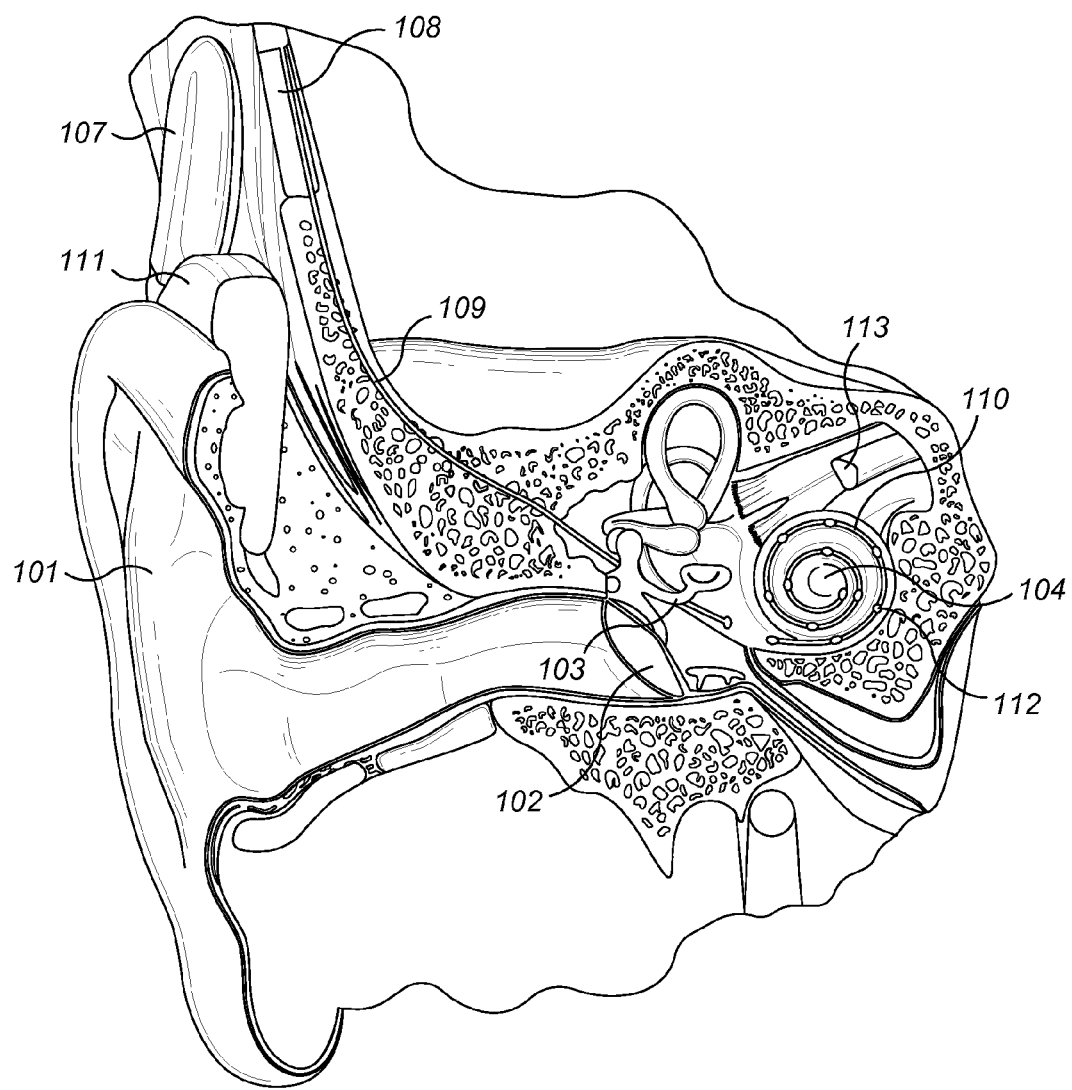
FIG. 1 shows various anatomical structures in a human ear and some components of a typical cochlear implant system.
Figure 2A:
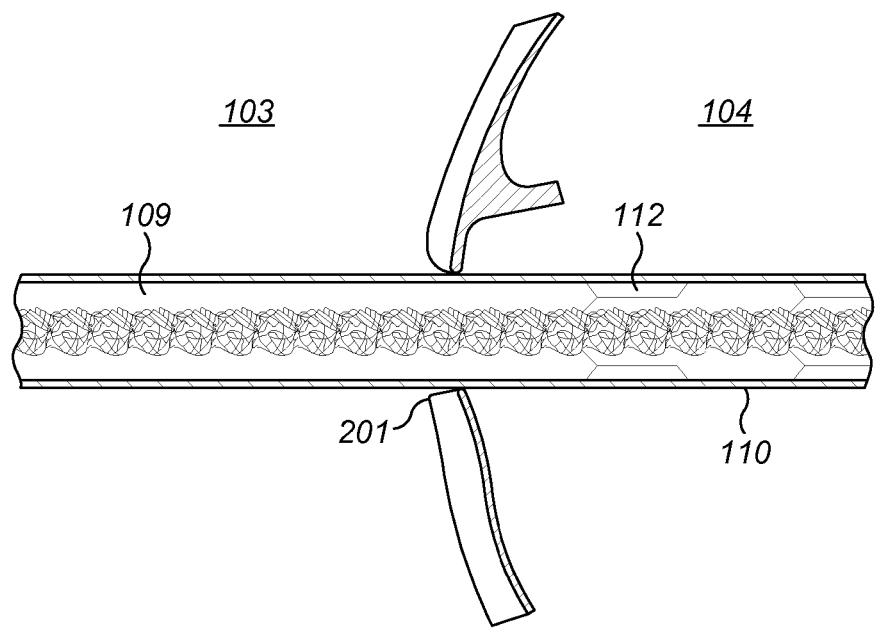
FIG. 2A shows structural details of a cochlear implant electrode arrangement at the electrode opening into the cochlea.
Figure 2B:
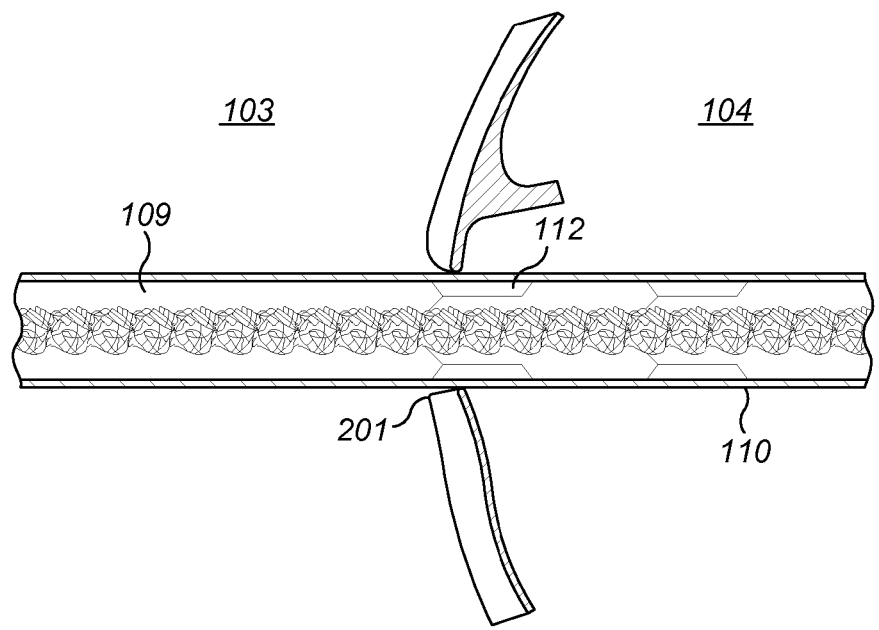
FIG. 2B shows how the proximal end of the intracochlear electrode array can retract back out of the electrode opening to pull the nearest stimulation contact back into the electrode opening.
Figure 3:
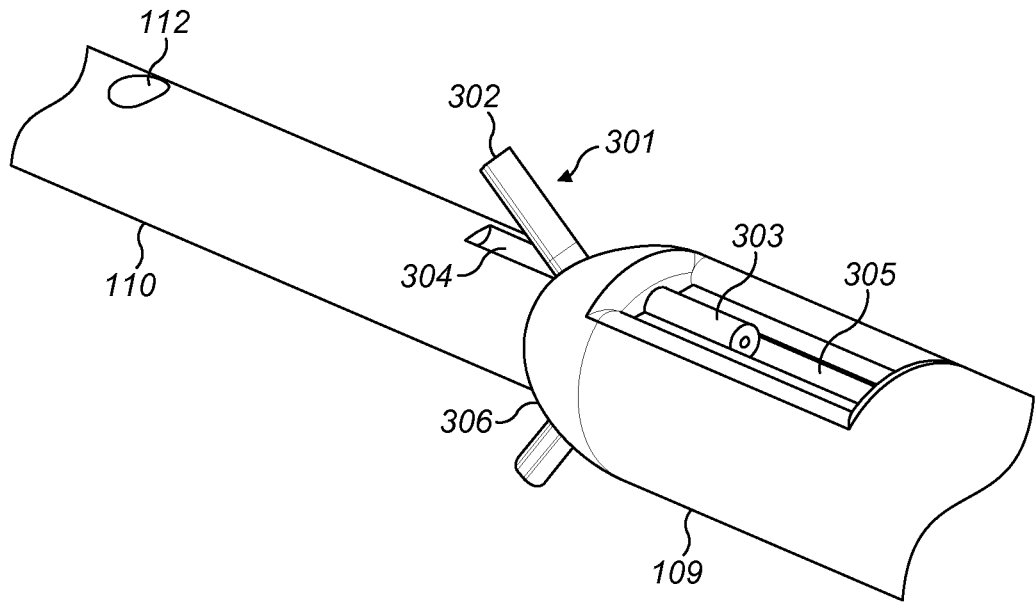
FIG. 3 shows structural details of a portion of an electrode arrangement with a retraction limiter according to an embodiment of the present invention.

FIG. 3 shows structural details of a portion of an electrode arrangement with a retraction limiter 301 according to one specific embodiment of the present invention. Like most conventional cochlear implant electrode arrangements, there is an extracochlear electrode lead 109 that has a proximal end couplable to an implanted signal processor (not shown) and an lead distal end 306 that enters an electrode opening in the outer surface of a cochlea. The electrode lead 109 is made of a resilient carrier material as is known in the art that contains electrode wires for carrying one or more cochlear stimulation signals. An intracochlear electrode array 110 has an array proximal end connected to the lead distal end 306 at the electrode opening, and an array distal end terminating within the implanted cochlea (not shown in FIG. 3). Like the electrode lead 109, the electrode array 110 is made of resilient carrier material that contains the electrode wires which each terminate in a stimulation contact 112 on the outer surface of the electrode array 110 that applies the cochlear stimulation signals to target neural tissue within the cochlea.

The electrode arrangement also includes at least one retraction limiter 301 made of preshaped silicone or swellable material with an extracochlear portion 303 that is fixed in place at the lead distal end 306, and an intracochlear portion 302 located at the array proximal end. FIG. 3 shows a specific arrangement with two opposing retraction limiters 301, but any number of multiple retraction limiters may be used depending on the intracochlear space available and taking care to avoid trauma to the basilar membrane. For example, there may be multiple retraction limiters 301 distributed radially around the outer surface of the proximal end of the electrode array 110.

The intracochlear portion 302 of the retraction limiter 301 shown in FIG. 3 is adapted to lie flat within a projection recess 304 during the surgical insertion procedure (to minimize insertion resistance and tissue trauma) and then is deformed away from the outer surface of the proximal end of the electrode array 110 after the surgical insertion to form an anti-retraction projection that resists post-surgical retraction of the proximal end of the electrode array 110 back through the electrode opening. The intracochlear portion 302 of the retraction limiter may be at least in part formed of or coated with swellable material. After surgical insertion, the intracochlear portion 302 comes into contact with the perilymph fluid in the cochlear and the swellable material expands and thereby supports forming the anti-retraction projection. In some embodiments there may also be an imaging marker within the retraction limiter 301 to prominently indicate the electrode opening in post-surgical imaging of the electrode arrangement.

Figure 4A:
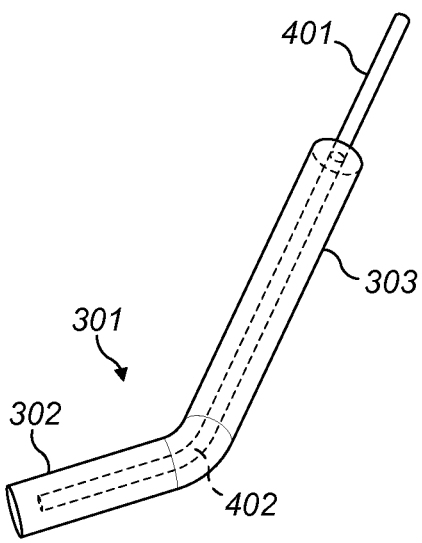
FIGS. 4A and 4B show structural details of the retraction limiter of FIG. 3.
Figure 4B:
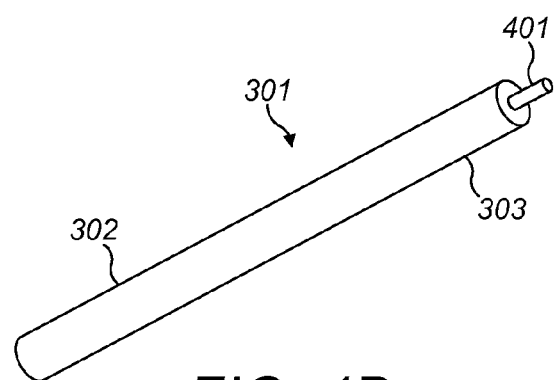

FIGS. 4A and 4B show structural details of the retraction limiter 301 of FIG. 3, which includes an internal stiffener channel 402 within the retraction limiter 301 along its longitudinal axis. In specific embodiments, the stiffener channel 402 may be open at both ends and run completely through the length of the retraction limiter 301, in which case it may be useful to add an end cap at one end to prevent bacterial infection from the middle ear into the cochlea. Such an end cap may temporarily removable to allow for drug delivery into the cochlear perilymph or sampling of the perilymph fluid. Or the stiffener channel 402 may run only partially within the retraction limiter 301 with the end of the extracochlear portion open and the end of the intracochlear portion 302 closed off.

Figure 5:
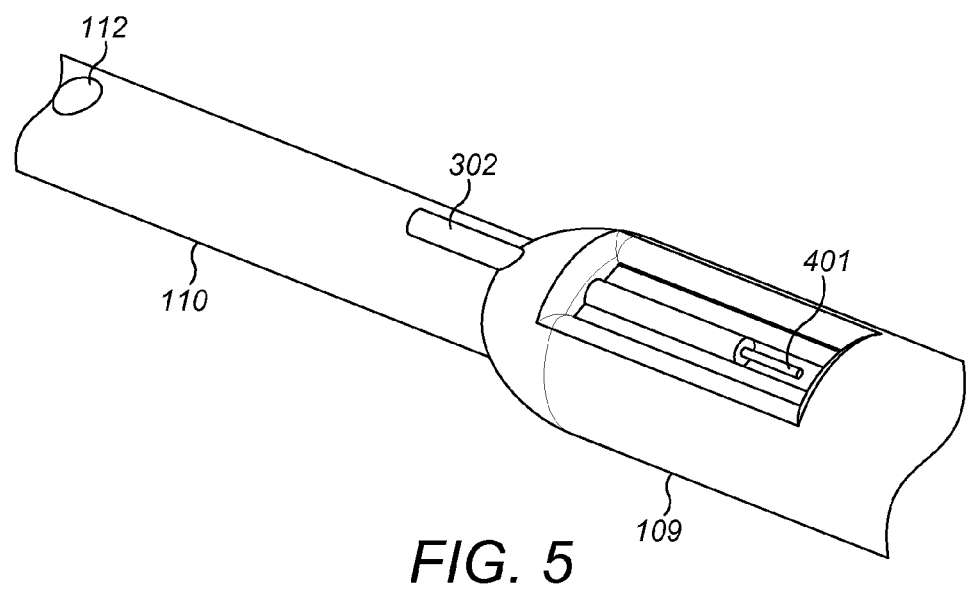
FIG. 5 shows structural details of an electrode arrangement with a retraction limiter containing an intra-surgical stiffener according to an embodiment of the present invention.

As shown in FIG. 4B and FIG. 5, during surgical insertion the stiffener channel 402 holds an insertion stiffener 401 that maintains the intracochlear portion 302 of the retraction limiter 301 straight and parallel against the outer surface of the proximal end of the electrode array 110. After insertion, the insertion stiffener 401 is withdrawn from the stiffener channel 402, which allows the intracochlear portion 302 of the retraction limiter 301 to deform away from the outer surface of the proximal end of the electrode array 110 to form an anti-retraction projection that resists post-surgical retraction of the proximal end of the electrode array 110 back through the electrode opening. For later explantation of the electrode array 110, the insertion stiffener 401 can be reinserted into the stiffener channel 402 to make it straight again to accommodate retraction of the electrode array 110 back out the electrode opening.

Figure 6A:
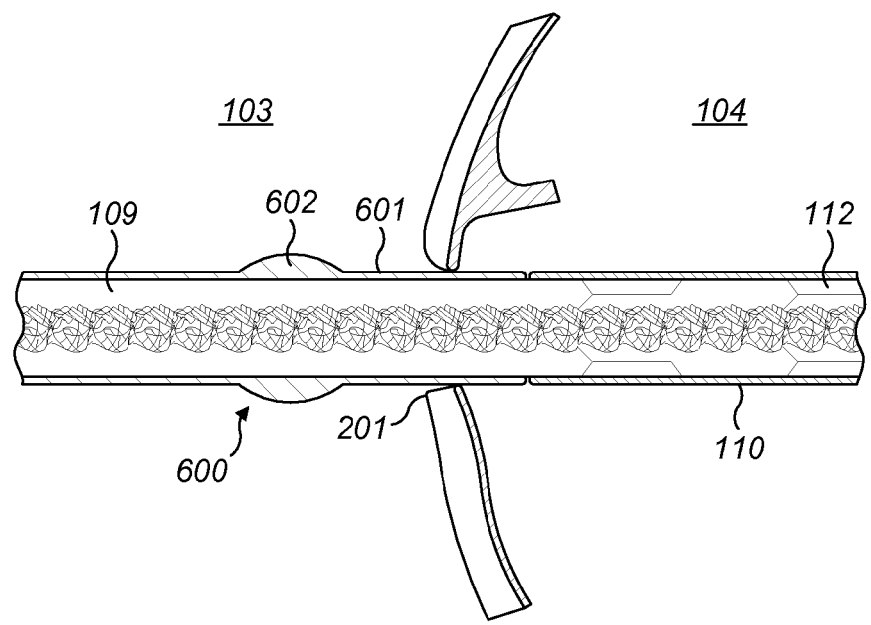
FIGS. 6A and 6B show structural details of a retraction limiter with an intracochlear portion adapted for post-insertion deformation to form anti-retraction projections according to an embodiment of the present invention.
Figure 6B:
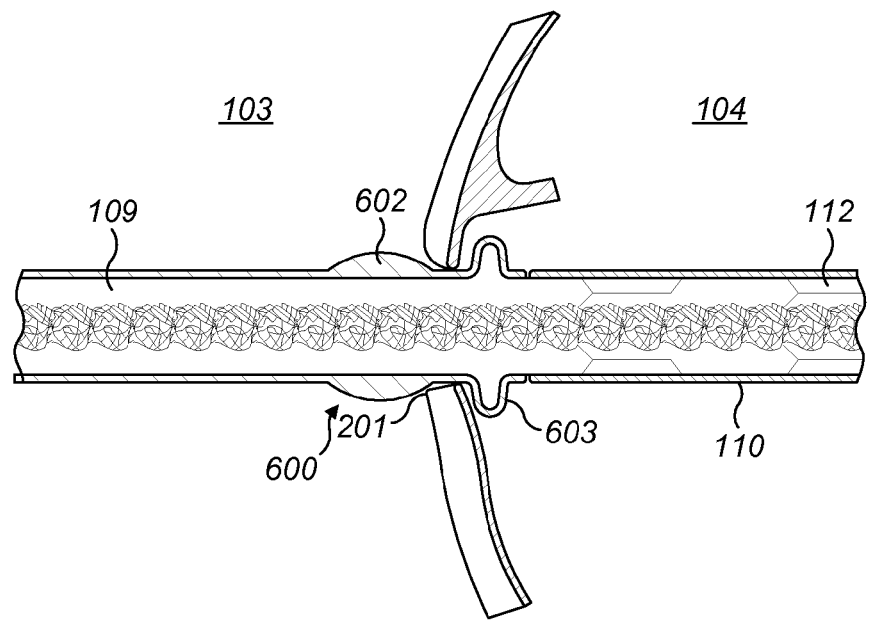

FIGS. 6A and 6B show structural details of another embodiment of a retraction limiter 600 at an electrode opening 201 in to the cochlea 104 where a distal end of the intracochlear portion 601 of the retraction limiter 600 is fixedly attached to the outer surface of the proximal end of the electrode array 110 (the far right side in FIGS. 6A and 6B). The remainder of the retraction limiter 600 including the remainder of the intracochlear portion 601 is separable from the outer surface. After full insertion of the electrode array through the electrode opening 201 into the cochlea 104, the extracochlear portion 602 of the retraction limiter 600 slides over the distal end of the electrode lead 109 and causes the separable part of the intracochlear portion 602 to deform out away from the outer surface of the proximal end of the electrode array 110 (by folding) as shown in FIG. 6B to form the anti-retraction projection 603. The intracochlear portion 601 of the retraction limiter may be at least in part formed of or coated with swellable material. After surgical insertion, the intracochlear portion 601 comes into contact with the perilymph fluid in the cochlear and the swellable material expands and thereby supports forming the anti-retraction projection 603. Similarly in one embodiment the extracochlear portion 602 may be at least in part formed or coated with swellable material. In some embodiments, the extracochlear portion 601 of the retraction limiter 600 may then be fixedly attached to the distal end of the electrode lead 109.

Figure 7A:
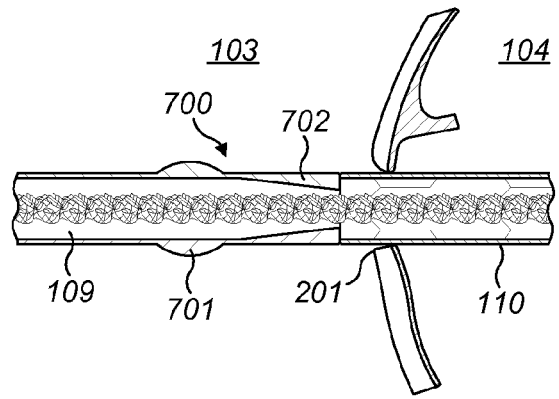
FIGS. 7A-7C show structural details of a retraction limiter using wedge-shaped intracochlear portions to form anti-retraction projections according to an embodiment of the present invention.
Figure 7B:
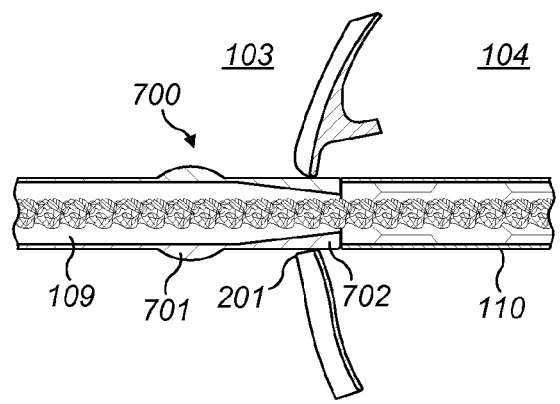
Figure 7C:
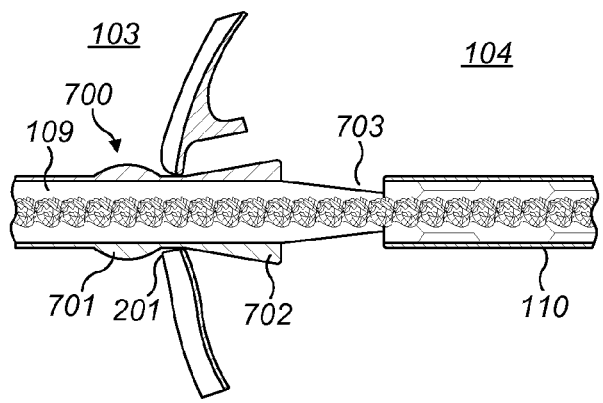

FIGS. 7A-7C show structural details of another embodiment of a retraction limiter 700 using wedge-shaped intracochlear portions 702 to form anti-retraction projections according to an embodiment of the present invention. During surgical insertion of the electrode array 110 into the cochlea 104, the wedge-shaped intracochlear portions 702 sit within corresponding wedge-shaped limiter receptacles 703 to lie flush with the outer surface of the proximal end of the electrode array 110, as shown in FIGS. 7A and 7B. Once insertion is completed, the retraction limiter 700 is pulled back to slide over the outer surface of the distal end of the electrode lead 109, pulling the wedge-shaped intracochlear portion 702 back out of the limiter receptacles 703 towards the electrode opening to form the anti-retraction projections. The intracochlear portion 702 of the retraction limiter may be at least in part formed of or coated with swellable material. After surgical insertion, the intracochlear portion 702 comes into contact with the perilymph fluid in the cochlear and the swellable material expands and thereby supports forming the anti-retraction projection. Similarly in one embodiment the extracochlear portion 701 may be at least in part formed or coated with swellable material. Once the anti-retraction projections have been formed, the extracochlear portion 701 of the retraction limiter 700 can then be securely fixed to the distal end of the electrode lead 109.

Figure 8:
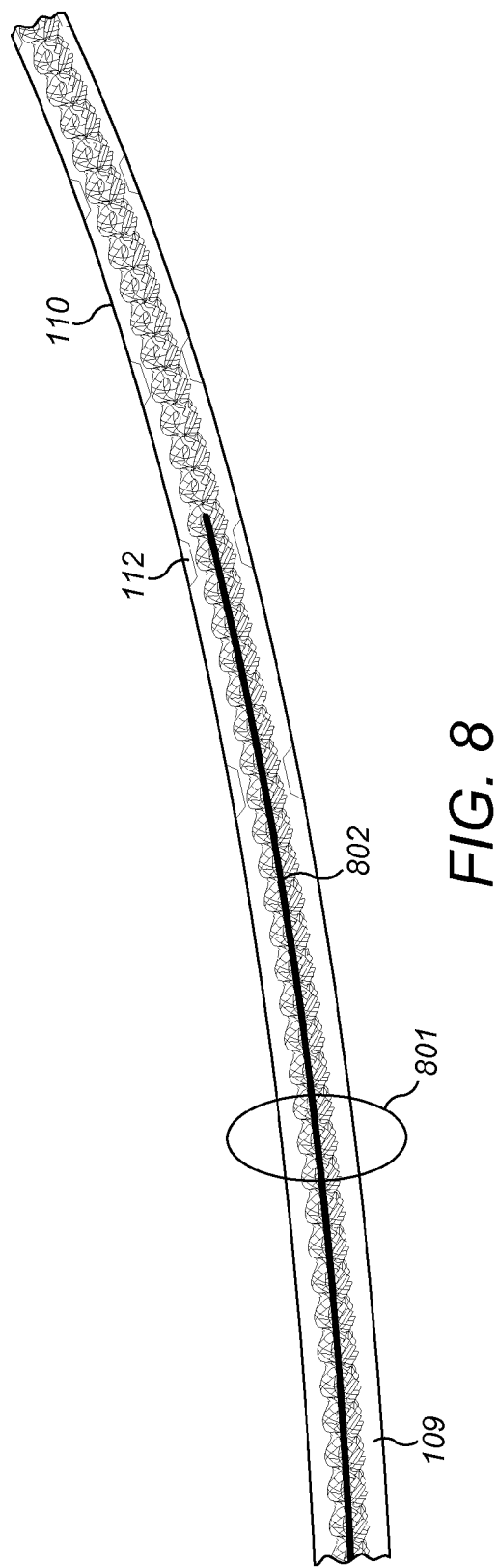
FIG. 8 shows a portion of a cochlear implant electrode with a deformable internal stiffener near the electrode opening that limits post-insertion retraction.

FIG. 8 shows a portion of a cochlear implant electrode arrangement with a deformable internal stiffener 802 near the electrode opening 801 that limits post-insertion retraction of the electrode array 110. Surgical insertion of the electrode array 110 into the spiral-shaped cochlea 104 bends the internal stiffener 802 which also keeps the proximal end of the electrode array 110 bent to prevent the springing back of the electrode array 110 back out of the electrode opening 801. The internal stiffener 802 may specifically be formed of a plastic deformable material which can be easily bent; for example, a deformable polymer material, a platinum ribbon, a nitinol rod, etc. In specific embodiments, the internal stiffener 802 can extend forward into the interior of the electrode array 110 beneath one or more of the stimulation contacts 112. In the specific embodiment shown in FIG. 8, the internal stiffener 802 extends under the two basal-most stimulation contacts 112. In other specific embodiments, the internal stiffener 802 may extend forward under four or more of the stimulation contacts 112.

Figure 9A:
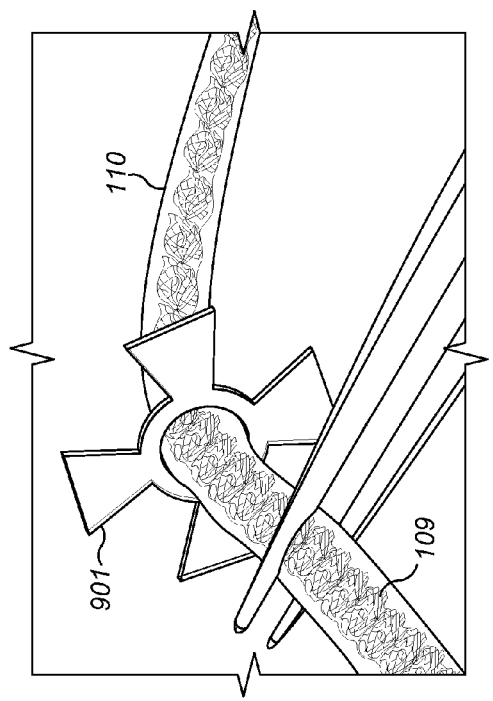
FIGS. 9A and 9B shows a portion of a cochlear implant electrode with a cross-shaped retraction limiter that limits post-insertion retraction.
Figure 9B:
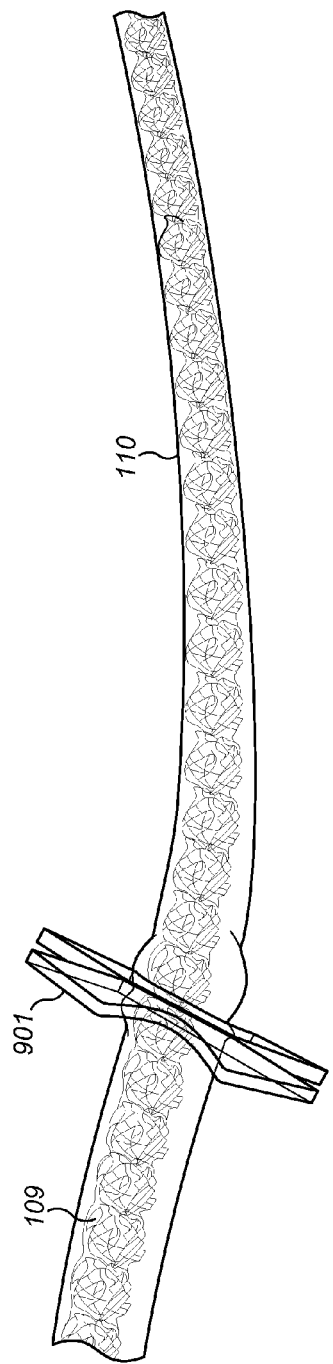
Figure 10A:
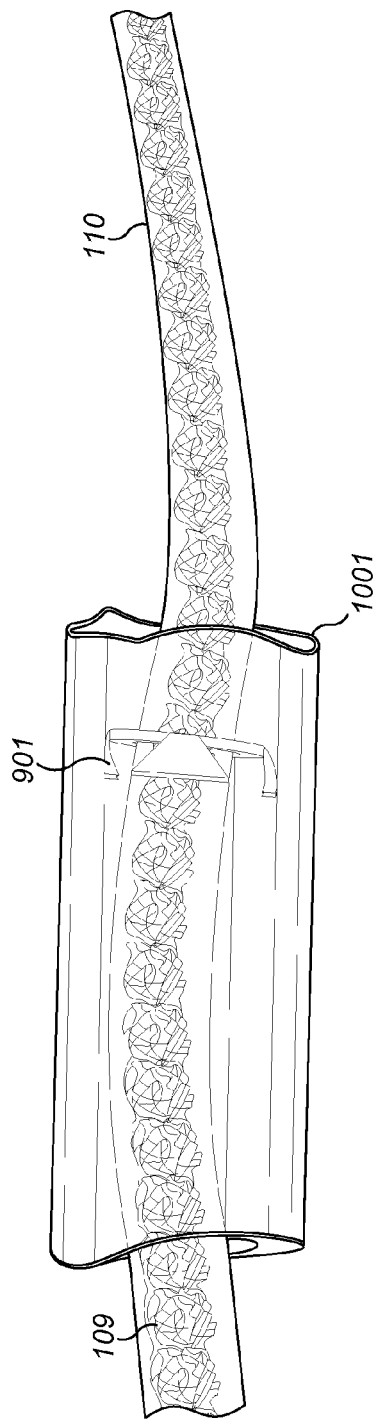
FIGS. 10A and 10B shows an insertion tube that fits over the retraction limiter of FIGS. 9A-9B during surgical insertion and which is slid back off the limiter after surgical insertion.
Figure 10B:
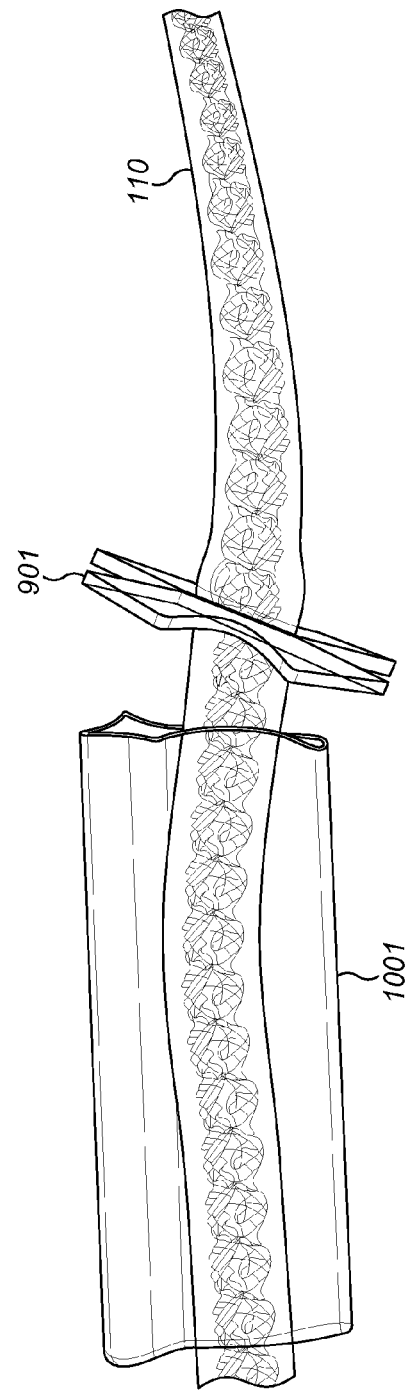

FIGS. 9A and 9B shows a portion of a cochlear implant electrode with a cross-shaped retraction limiter 901 at the electrode opening between the inserted electrode array 110 and the middle ear electrode lead 109. The retraction limiter 901 is made of resilient silicone material that is compressed during the surgical insertion to fit through the electrode opening into the interior volume of the cochlea. When insertion is complete, the cross-shaped retraction limiter 901 is released to expand back into its natural shape which limits post-insertion retraction of the electrode array 110 back through the electrode opening. For example, as shown in FIGS. 10A and 10B, the retraction limiter 901 can be compressed within an insertion tube 1001 during the surgical insertion, and then after insertion, the insertion tube 1001 is slid back off the retraction limiter 901.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable electrode arrangement for a cochlear implant system, comprising:
    an extracochlear electrode lead for carrying one or more cochlear stimulation signals, the electrode lead having a lead proximal end couplable to an implanted signal processor, and a lead distal end configured to enter an electrode opening in the outer surface of a cochlea;
    an intracochlear electrode array for insertion into the cochlea, the electrode array having:
        i. an array proximal end configured to be connected to the lead distal end at the electrode opening,
        ii. an array distal end configured for terminating within the cochlea, and iii. an outer surface with a plurality of stimulation contacts for applying the cochlear stimulation signals to target neural tissue within the cochlea; and at least one retraction limiter having an extracochlear portion located at the lead distal end and an intracochlear portion located at the array proximal end;

wherein a distal end of the intracochlear portion of the at least one retraction limiter is fixedly attached to the outer surface of the array proximal end, and wherein the remainder of the intracochlear portion is separable from the outer surface of the array proximal end, whereby sliding of the extracochlear portion of the at least one retraction limiter over the lead distal end causes the separable part of the intracochlear portion to deform out away from the outer surface of the array proximal end to form an anti-retraction projection configured for preventing post-surgical retraction of the array proximal end back through the electrode opening.

2. The electrode arrangement according to claim 1, wherein the extracochlear portion of the at least one retraction limiter is adapted for fixed attachment to the lead distal end after sliding.

3. The electrode arrangement according to claim 1, wherein the at least one retraction limiter further includes an imaging marker configured to prominently indicate the location of the retraction limiter after implantation relative to patient physiology in post-surgical imaging of the electrode arrangement.

4. The electrode arrangement according to claim 1, wherein the at least one retraction limiter is made at least in part of a swellable material that expands in response to fluid contact.

5. The electrode arrangement according to claim 4, wherein the swellable material comprises a hydrogel material.

6. The electrode arrangement according to claim 1, wherein the electrode arrangement includes a plurality of retraction limiters.

7. An implantable electrode arrangement for a cochlear implant system, comprising:

an extracochlear electrode lead for carrying one or more cochlear stimulation signals, the electrode lead having a lead proximal end couplable to an implanted signal processor, and a lead distal end configured to enter an electrode opening in the outer surface of a cochlea;

an intracochlear electrode array for insertion into the cochlea, the electrode array having:
  i. an array proximal end configured to be connected to the lead distal end at the electrode opening,
  ii. an array distal end configured for terminating within the cochlea, and
  iii. an outer surface with a plurality of stimulation contacts for applying the cochlear stimulation signals to target neural tissue within the cochlea; and at least one retraction limiter having an extracochlear portion located at the lead distal end and an intracochlear portion located at the array proximal end;

wherein the intracochlear portion of the at least one retraction limiter is adapted for deformation away from the outer surface of the array proximal end after surgical insertion of the electrode array into the cochlea so as to form an anti-retraction projection configured for preventing post-surgical retraction of the array proximal end back through the electrode opening; and wherein the intracochlear portion of the retraction limiter is wedge-shaped, and wherein the outer surface of the array proximal end includes a corresponding wedge-shaped limiter receptacle adapted to contain the intracochlear portion during surgical insertion of the electrode array into the cochlea, and wherein the intracochlear portion is adapted for sliding back out of the limiter receptacle towards the electrode opening after the surgical insertion to form the anti-retraction projection.

8. An implantable electrode arrangement for a cochlear implant system, comprising:

an extracochlear electrode lead for carrying one or more cochlear stimulation signals, the electrode lead having a lead proximal end couplable to an implanted signal processor, and a lead distal end configured to enter an electrode opening in the outer surface of a cochlea;

an intracochlear electrode array for insertion into the cochlea, the electrode array having:
  i. an array proximal end configured to be connected to the lead distal end at the electrode opening,
  ii. an array distal end configured for terminating within the cochlea, and
  iii. an outer surface with a plurality of stimulation contacts for applying the cochlear stimulation to et neural tissue within the cochlea; and at least one retraction limiter having an extracochlear portion located at the lead distal end and an intracochlear portion located at the array proximal end;

wherein the intracochlear portion of the at least one retraction limiter is adapted for deformation away from the outer surface of the array proximal end after surgical insertion of the electrode array into the cochlea so as to form an anti-retraction projection configured for preventing post-surgical retraction of the array proximal end back through the electrode opening; and wherein the at least one retraction limiter includes an internal stiffener channel configured to:
  i. contain an insertion stiffener that holds the intracochlear portion of the retraction limiter straight against the outer surface of the array proximal end during surgical insertion of the electrode array into the cochlea, and
  ii. allow the intracochlear portion of the retraction limiter to deform away from the outer surface of the array proximal end to form the anti-retraction projection when the insertion stiffener is withdrawn from the stiffener channel after surgical insertion of the electrode array into the cochlea.

9. A cochlear implant system having an electrode arrangement according to any of claims 1-7.

* * * * *

UNITED STATES PATENT AND TRADEMARK OFFICE
CERTIFICATE OF CORRECTION

PATENT NO. : 9,295,831 B2
APPLICATION NO. : 14/618000
DATED : March 29, 2016
INVENTOR(S) : Hagr et al.

It is certified that error appears in the above-identified patent and that said Letters Patent is hereby corrected as shown below:

Claims
In Col. 8, line 30, claim 8
replace "to et neural"
with --signals to target neural--

Signed and Sealed this
Fourteenth Day of June, 2016

Michelle K. Lee
*Director of the United States Patent and Trademark Office*